(12) United States Patent
Cuconati et al.

(10) Patent No.: US 8,609,668 B2
(45) Date of Patent: Dec. 17, 2013

(54) SUBSTITUTED TRIAZOLO[1,5-A]PYRIMIDINES AS ANTIVIRAL AGENTS

(75) Inventors: Andrea Cuconati, Oreland, PA (US); Timothy M. Block, Doylestown, PA (US); Xiaodong Xu, Doylestown, PA (US)

(73) Assignees: Philadelphia Health & Education Corporation, Philadelphia, PA (US); Institute For Hepatitis and Virus Research, Doylestown, PA (US)

( * ) Notice: Subject to any disclaimer, the term of this patent is extended or adjusted under 35 U.S.C. 154(b) by 1051 days.

(21) Appl. No.: 12/299,532

(22) PCT Filed: May 4, 2007

(86) PCT No.: PCT/US2007/068241
§ 371 (c)(1),
(2), (4) Date: Nov. 4, 2008

(87) PCT Pub. No.: WO2007/131168
PCT Pub. Date: Nov. 15, 2007

(65) Prior Publication Data
US 2009/0088397 A1    Apr. 2, 2009

Related U.S. Application Data

(60) Provisional application No. 60/797,581, filed on May 4, 2006.

(51) Int. Cl.
*A61K 31/519* (2006.01)
*A61P 31/20* (2006.01)
*C07D 487/04* (2006.01)

(52) U.S. Cl.
USPC ..................... 514/259.3; 544/254

(58) Field of Classification Search
USPC ..................... 514/259.3
See application file for complete search history.

(56) References Cited

PUBLICATIONS

Andotra et. al., Indian Journal of Chemistry, Section B: Organic Chemistry Including Medicinal Chemistry, 2004, 43B(3), 667-669.*
Andotra et. al. (Indian Journal of Chemistry, Section B: Organic Chemsitry Including Medicinal Chemistry, 2004, 43B(3), pp. 667-669).*
Kukka (HBV Advocate, HBV/HIV Coinfection: What You Need to Know, 2004, <http://www.hbadvocate.org/hepatitis/hepB/HBV_HIV_coinfection_FS.html >, downloaded Dec. 17, 2011.*

* cited by examiner

*Primary Examiner* — Susanna Moore
(74) *Attorney, Agent, or Firm* — Woodcock Washburn, LLP

(57) ABSTRACT

A pharmaceutical composition comprising an effective amount of a compound of formulas (I-III) and a pharmaceutically acceptable carrier. Methods for treating a hepatitis virus in a patient comprising administering an effective amount of the compound of formulas (I-III) are also presented.

2 Claims, 6 Drawing Sheets

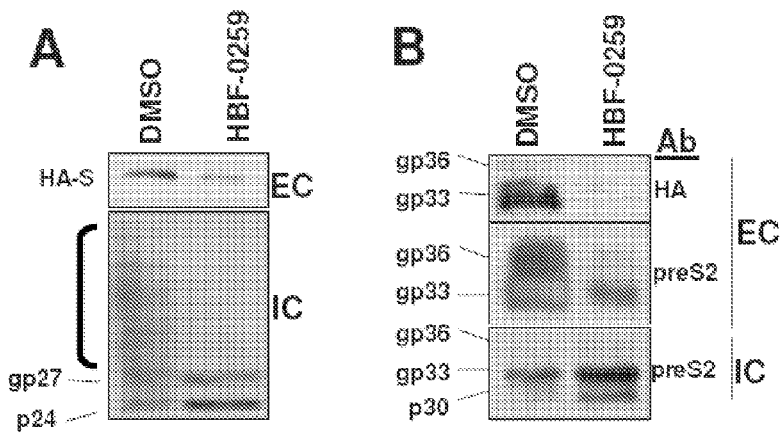
Figures 5a and 5b.
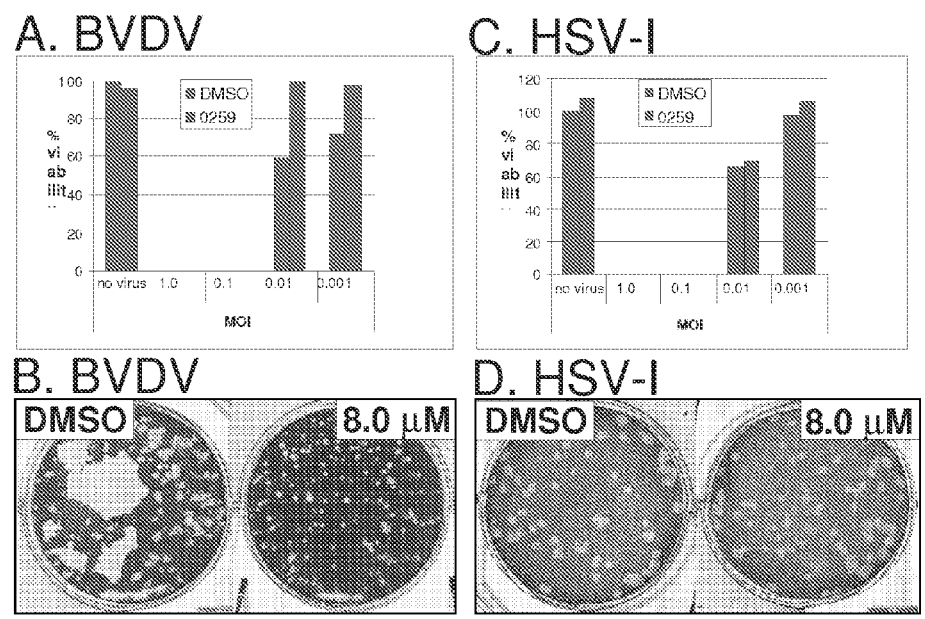
Figures 6a-d.

| CMPD | R1 | R2 | EC50 | CC50 | SI |
|---|---|---|---|---|---|
| 3027 | (phenyl, Cl, R) | (R, phenyl, ethyl) | 2.8 | 49.9 | 53.5 |
| 4567 | (phenyl, Cl, R) | (R, phenyl, methyl) | 2.8 | 37.5 | 13.4 |
| 4222 | (phenyl, Cl, F, R) | (R, phenyl, I) | 4.9 | 40.1 | 8.2 |
| 4602 | (phenyl, F, R) | (R, phenyl, methyl) | 9.1 | >50 | >5.49 |
| 4214 | (phenyl, Cl, F, R) | (R, phenyl, O) | 12.0 | UD | ND |
| 2160 | (phenyl, Br, F, R) | (R, phenyl, Cl) | 33.1 | >50 | >1.5 |
| 4564 | (phenyl, Cl, R) | (R, phenyl, methyl) | >50 | 49.6 | <1.0 |
| 1573 | (phenyl, F, R) | (R, phenyl, Cl) | >50 | UD | ND |
| 4498 | (phenyl, Cl, R) | (R, phenyl, I) | NA | >50 | ND |
| 1203 | (phenyl, F, R) | (R, phenyl, I) | NA | UD | ND |

Figure 7.

SUBSTITUTED TRIAZOLO[1,5-A]PYRIMIDINES AS ANTIVIRAL AGENTS

CROSS-REFERENCE TO RELATED APPLICATIONS

This application claims priority under 35 U.S.C. §119(e) to U.S. Provisional Application Ser. No. 60/797,581, which was filed on May 4, 2006. The disclosure of which is incorporated herein by reference.

BACKGROUND OF THE INVENTION

Hepatitis B is one of the world's most prevalent diseases. Although most individuals seem to resolve the infection following acute symptoms, approximately 30% of cases become chronic. According to current estimates, 350-400 million people worldwide have chronic hepatitis B, leading to 500,000-1,000,000 deaths per year due largely to the development of hepatocellular carcinoma, cirrhosis, and other complications. Despite the availability of an effective vaccine, immunoglobulin therapy, interferon, and antiviral drugs, hepatitis B remains a major global health problem.

The causative agent is hepatitis B virus (HBV), a small DNA virus that is considered to be the prototypical member of the hepadnaviridae. HBV is an enveloped virus with an unusual mode of replication, centering on the establishment of a covalently closed circular DNA (cccDNA) copy of its genome in the host cell nucleus. This episomal form is established from conversion of the partially double stranded circular DNA (relaxed circular, or rcDNA) genome upon initial infection, and functions as the template for all HBV mRNAs. Unlike the mechanisms of most other DNA viruses, HBV cccDNA replicates through retrotranscription of a 1.1 genome unit-length RNA copy (pregenomic, or pgRNA) which is originally transcribed from the cccDNA template, and which is acted upon by a virus-encoded polymerase to yield progeny rcDNA. HBV DNA synthesis is coupled to assembly of its capsid, and most copies of the encapsidated genome then efficiently associate with the envelope proteins for virion assembly and secretion; a minority of these genomes are shunted to the nucleus where they are converted to cccDNA, thus amplifying levels of the episome.

As the only enzyme encoded by HBV, the polymerase has been well-exploited as a target for antiviral drug development, with four nucleoside-analogous polymerase inhibitors already FDA-approved, and others in development. Mutations in the primary sequence of the polymerase that confer resistance to lamivudine and adefovir have been identified clinically, and underlie a rebound of serum virus titers that 70% of treated patients experience within three years of starting lamivudine therapy. Although resistance to telbivudine, adefovir and entecavir occurs more rarely, it has been recorded. α-Interferon is the other major therapy available for hepatitis B, but is limited by poor long-term response and debilitating side effects. Hence, there is certainly a medical need for treatments with improved characteristics, and for a diversity of approaches in developing HBV therapies.

Aside from being a critical structural component of the virion, the HBV envelope is a major factor in the disease process. In chronically infected individuals, serum levels of HBV surface antigen (HBsAg) can be as high as 400 μg/ml, driven by the propensity for infected cells to secrete non-infectious subviral particles at levels far in excess of infectious (Dane) particles. HBsAg comprises the principal antigenic determinant in HBV infection and is composed of the small, middle and large surface antigens (S, M, and L, respectively). These proteins are produced from a single open reading frame as three separate N-glycosylated polypeptides through utilization of alternative transcriptional start sites (for L and M/S mRNAs) and initiation codons (for L, M and S).

Although the viral polymerase and HBsAg perform very different functions, both are essential proteins for the virus to complete its life cycle and be infectious. That is, HBV lacking HBsAg is completely defective and cannot infect or cause infection. HBsAg is needed to protect the virus nucleocapsid, to begin the infectious cycle, and to mediate morphogenesis and secretion of newly forming virus from the infected cell.

People who are chronically infected with HBV are usually characterized by readily detectable levels of circulating antibody specific to the viral capsid (HBc), with little, if any detectable levels of antibody to HBsAg. There is some evidence that chronic carriers do produce antibodies to HBsAg, but these antibodies are complexed with the circulating HBsAg, which can be present in milligram per milliliter amounts in a chronic carrier's circulation.

Reducing the amount of circulating levels of HBsAg might permit whatever anti-HBsAg is present to gain a foothold and enable the antibody to manage the infection. Moreover, even if nucleocapsids, free of HBsAg, were to be expressed or secreted in to the circulation, perhaps as a result of cell death, the high levels of anti-HBc would be expected to quickly complex with them and result in their clearance.

A study of duck hepatitis B virus (DHBV) has indicated that the presence of subviral particles in a culture of infected hepatocytes may have a transactivating function on viral genomic replication. In addition, a long-held tenet of HBV biology is that this circulating surface antigen functions to suppress virus-specific immune response. In chronic woodchuck hepatitis virus (WHV) infection, a reduction of antigenemia through clevudine treatment resulted in a positive response to vaccination indicating that circulating antigen may indeed suppress the immune response. Furthermore, the scarcity of virus-specific cytotoxic T lymphocytes (CTLs) that is a hallmark of chronic WHV and HBV infection may be due to repression of MHC I presentation by intracellular expression of L and M in infected hepatocytes. Existing FDA-approved therapies do not significantly affect HBsAg levels in the serum.

SUMMARY OF THE INVENTION

The present invention relates to pharmaceutical compositions of an effective amount of a compound selected from Formulas I, II, III, and mixtures thereof:

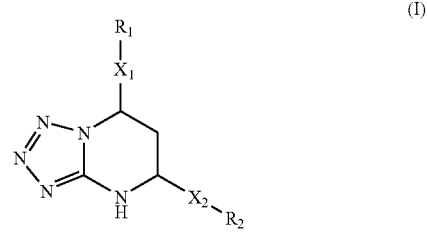

(I)

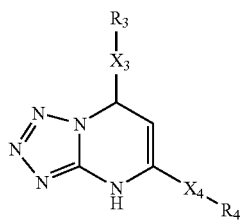

(II)

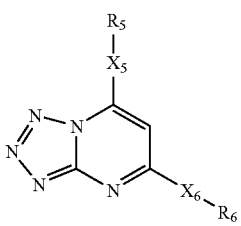

(III)

wherein $R_1$-$R_6$ are independently phenyl or Het, wherein each phenyl or Het is optionally substituted with at least one substituent independently selected from the group consisting of $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, aryl, halo, $OR_a$, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, and Het, wherein $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$X_1$-$X_6$ are independently a bond or a saturated or unsaturated alkylene group;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

m is 0, 1, or 2;

n is 0, 1, 2, 3, or 4;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative and (b) a pharmaceutically acceptable carrier.

Also provided are compounds of Formula IV, V, or VI:

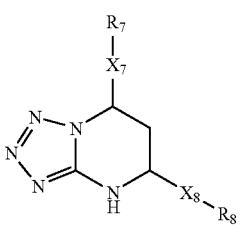

(IV)

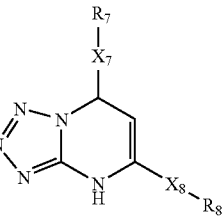

(V)

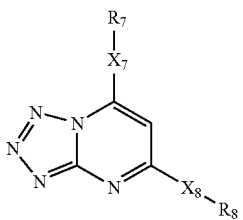

(VI)

wherein $R_7$ and $R_8$ are independently phenyl or Het, wherein each phenyl or Het is optionally substituted with at least one substituent independently selected from the group consisting of $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, aryl, halo, $OR_a$, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, and Het, wherein $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$X_7$ and $X_8$ are independently a bond or a saturated or unsaturated alkylene group;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

m is 0, 1, or 2;

n is 0, 1, 2, 3, or 4; or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative;

provided that the compound is a compound of formula VI when $R_7$ is methyl, p-MeOC$_6$H$_4$, or p-BrC$_6$H$_4$, $R_8$ is unsubstituted phenyl, and $X_7$ and $X_8$ are each a single bond; or when $R_7$ is unsubstituted phenyl, $R_8$ is unsubstituted phenyl, methyl, p-MeOC$_6$H$_4$, or p-BrC$_6$H$_4$, and $X_7$ and $X_8$ are each a single bond; and the compound is a compound of formula IV or VI when $R_7$ is H, $R_8$ is unsubstituted phenyl, p-MeOC$_6$H$_4$, or p-BrC$_6$H$_4$, and $X_7$ and $X_8$ are each a single bond; when $R_7$ is p-ClC$_6$H$_4$, $R_8$ is unsubstituted phenyl, and $X_7$ and $X_8$ are each a single bond; or when $R_7$ is unsubstituted phenyl, $R_8$ is p-ClC$_6$H$_4$, and $X_7$ and $X_8$ are each a single bond.

Methods for treating a hepatitis virus in a patient by administering an effective amount of a compound of formulas I-III to a patient in need thereof are also presented. In one embodiment, the method includes administering to the patient an effective amount of a compound of formulas I-III that reduces the serum level of hepatitis B surface antigen (HBsAg) in the patient.

BRIEF DESCRIPTION OF THE DRAWINGS

FIGS. 5a-b show that HBF-0259 inhibits secretion of exogenously expressed S and M. (A) HepG2 cells were transfected with plasmid pNI2.SHA, encoding S-HA, and treated with 4 µM HBF-0259 or DMSO as indicated, for 48 hrs. Culture supernatants and cell monolayers were harvested and analyzed by Western blotting for S-HA. p24 and gp27 represent non-glycosylated and glycosylated S-HA, respectively, as predicted by their migration in SDS-PAGE. (B) HepG2 cells were transfected with plasmid pTRE-MSHA, encoding M-HA, and treated as in (A), and analyzed by Western blotting for M-HA, or preS2 using appropriate antibody (Ab). p30, gp33 and gp36 represent non-glycosylated, singly glycosylated, and double glycosylated M-HA. (EC, extracellular; IC, intracellular);

FIGS. 6a-d represent an antiviral spectrum of HBF-0259. (A) MDBK cells were infected with indicated MOI of BVDV on 96-well microtiter plates, in of HBF-0259 or DMSO, and processed. Values for percent viability were average of quadruplicate samples. Percent viability was calculated by setting average of uninfected, DMSO-treated controls at 100%. (B) MDBK cells were seeded onto 6-well plates and infected with an approximate total of 100 PFU/ml of BVDV, under semisolid overlay, in the presence of HBF-0259, or DMSO. Plaques were visualized by crystal violet staining. (C) Vero cells were infected with indicated MOI of HSV1 on microtiter plates, and processed as in (A). (D) Vero cells were infected with an approximate total of 100 PFU of HSV-1, and treated and processed as in (B); and FIG. 7 is a table providing results of nascent SAR analysis of HBF-0259. $R_1$ and $R_2$ represent substituent groups as indicated in FIG. 2a. R represents the central tetrahydro-tetrazolo-pyrimidine group. (NA, not active. UD, undetectable toxicity. ND, not determined).

DETAILED DESCRIPTION OF THE INVENTION

Figure 1:
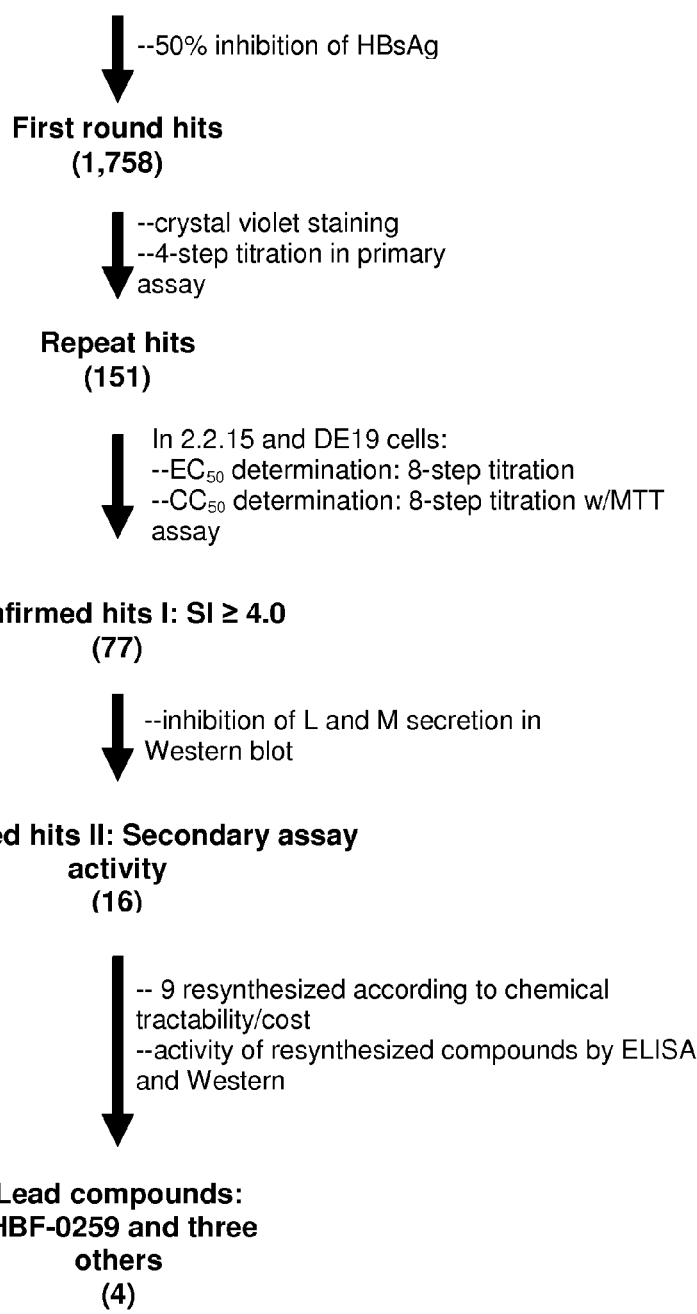
FIG. 1 is an illustration of a high throughput screening paradigm. Parentheses represent the number of compounds surviving selection at that step.

The present invention relates to compositions and methods for treating a hepatitis virus in a patient.

As used above, and throughout the description of the invention, the following terms, unless otherwise indicated, shall be understood to have the following meanings:

"Patient" means a mammal including a human.

"Effective amount" means an amount of compound of the present invention effective for treating a hepatitis virus, and thus producing the desired therapeutic effect.

"Treat" or "treatment" or "treating" mean to lessen, eliminate, inhibit, improve, alter, or prevent a disease or condition, for example by administration of compound of the present invention.

"Alkyl" means aliphatic hydrocarbon group which may be branched or straight-chained having about 1 to about 10 carbon atoms. Preferred alkyl is "lower alkyl" having about 1 to about 3 carbon atoms; more preferred is methyl. Branched means that one or more lower alkyl groups such as methyl, ethyl, or propyl are attached to a linear alkyl chain. The alkyl group is also optionally substituted by alkoxy, halo, carboxy, hydroxy or $R_eR_fN$— (wherein $R_e$, and $R_f$ are independently hydrogen or alkyl, or $R_e$, and $R_f$ taken together with the nitrogen atom to which $R_e$, and $R_f$ are attached form azaheterocyclyl); and preferably optionally substituted by fluoro. Examples of alkyl include methyl, fluoromethyl, difluoromethyl, trifluoromethyl, ethyl, n-propyl, isopropyl, butyl, sec-butyl, t-butyl, amyl and hexyl.

"Cycloalkyl" means a non-aromatic monocyclic ring system of about 3 to about 7 carbon atoms. Preferred monocyclic cycloalkyl rings include cyclopentyl, cyclohexyl, and cycloheptyl; more preferred are cyclohexyl and cyclopentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, alkoxycarbonyl or $Y_1Y_2NCO$—, wherein $Y_1$ and $Y_2$ are independently hydrogen or alkyl.

"Het" is a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het includes "heteroaryl," which encompasses about a 5- to about a 10-membered aromatic monocyclic or bicyclic hydrocarbon ring system in which one to three of the atoms in a monocyclic ring system, and one to four of the atoms in a bicyclic ring system, is/are elements(s) other than carbon, for example nitrogen, oxygen or sulfur. The "heteroaryl" may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazoly, pyrazolyl, furazanyl, pyrrolyl, imidazo[2,1-b]thiazolyl, benzofurzanyl, indolyl, azaindolyl, benzimidazolyl, benzothienyl, quinolinyl, imidazolyl and isoquinolinyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and caproyl.

"Alkoxy" means an alkyl-O— group in which the alkyl group is as previously described. Preferred alkoxy is "lower alkoxy" having about 1 to about 3 carbon atoms; more preferred is methoxy. The alkoxy may be optionally substituted by one or more alkoxy, carboxy, alkoxycarbonyl, carboxyaryl or $R_eR_fN$— (wherein $R_e$, and $R_f$ are as defined above). Exemplary alkoxy groups include methoxy, ethoxy, n-propoxy, i-propoxy, n-butoxy, heptoxy, 2-(morpholin-4-yl)ethoxy and 2-(ethoxy)ethoxy.

"Aryloxy" means aryl-O— group in which the aryl group is as previously described.

"Acyloxy" means and acyl-O— group in which the acyl group is as previously described.

"Carboxy" means a HO(O)C— (carboxylic acid) group.

"$R_eR_fN$-" means a substituted or unsubstituted amino group, wherein $R_e$ and $R_f$ are as previously described. Exemplary groups include amino ($H_2N$—), methylamino, ethylmethylamino, dimethylamino and diethylamino.

"$R_eR_fNCO$—" means a substituted or unsubstituted carbomoyl group, wherein $R_e$ and $R_f$ are as previously described. Exemplary groups are carbamoyl ($H_2NCO$—) are dimethylaminocarbamoyl ($Me_2NCO$—).

"AcylR$_e$N-" means an acylamino group wherein $R_e$ and acyl are as defined herein.

"Halo" means fluoro, chloro, bromo, or iodo. Preferred are fluoro, chloro or bromo, and more preferred are fluoro or chloro.

"Prodrug" means a form of the compound of formula I suitable for administration to a patient without undue toxicity, irritation, allergic response, and the like, and effective for their intended use. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, et., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Substituent of a ring structure" means any atom or group of atoms bonded to a ring in a molecule.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

One embodiment of the present invention is a pharmaceutical composition, wherein $R_1$ and $R_2$ of formula I are phenyl independently optionally substituted with at least one substituent independently selected from $(C_{1-7})$alkyl, halo, and $OR_a$.

Another embodiment of the invention is a pharmaceutical composition, wherein $X_1$ and $X_2$ are each a bond and $R_1$ is

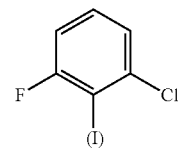

and $R_2$ is

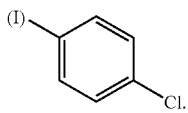

The compound according to this embodiment is also referred to herein as "HBF-0259" or "7-(2-chloro-6-fluoro-phenyl)-5-(4-chloro-phenyl)-4,5,6,7-tetrahydro-tetrazolo[1,5-a]pyrimidine."

It is to be understood that this invention covers all appropriate combinations of the particular and preferred groupings referred to herein.

The compounds of this invention may be prepared by employing procedures known in the literature starting from known compounds or readily prepared intermediates. For example, the preparation of partially hydrogenated aromatic substituted tetrazolo[1,5-a]pyrimidines is disclosed in Desenko, S. M. et al., Chemistry of Heterocyclic Compounds, vol. 37, pp. 747-54 (2001). Compounds can also be obtained from ChemDiv, Inc. (San Diego, Calif.).

The compounds of formulas I-III can be included in pharmaceutical compositions to treat, for example, a hepatitis virus in a patient. Examples of hepatitis viruses include viruses of the hepadnaviridae family, for example hepatitis B virus, and hepatitis delta virus.

In one embodiment, the pharmaceutical composition further includes an antiviral compound. In another embodiment, the antiviral compound is selected from nucleoside antiviral compounds, nucleotide antiviral compounds, and mixtures thereof.

Also provided is a method for treating a hepatitis virus in a patient by administering an effective amount of the compound of formulas I-III to a patient in need thereof. An additional method for treating a hepatitis virus in a patient includes administering to the patient an effective amount of a compound of formula I that reduces the serum level of hepatitis B surface antigen (HBsAg) in the patient.

In practice, a composition containing a compound of formulas I-III may be administered in any variety of suitable forms, for example, by inhalation, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of formulas I-III may be presented in forms permitting administration by the most suitable route. The invention also relates to administering compositions containing a compound of formulas I-III which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formulas I-III in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formulas I-III may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formulas I-III as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of formulas I-III in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of formulas I-III may be used. The compound of formulas I-III may be also incorporated in a gel or matrix base for application in a patch, which would allow a controlled release of compound through transdermal barrier.

For administration by inhalation, the compound of formulas I-III may be dissolved or suspended in a suitable carrier for use in a nebulizer or a suspension or solution aerosol, or may be absorbed or adsorbed onto a suitable solid carrier for use in a dry powder inhaler.

The percentage of compound of formulas I-III in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of formulas I-III used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of formulas I-III may be administered 1 to 4 times per day. Of course, for other patients, it will be necessary to prescribe not more than one or two doses per day.

The following non-limiting examples set forth hereinbelow illustrate certain aspects of the invention.

EXAMPLES

Cell culture, viruses, antibodies, and plasmids. For assay development and high-throughput screening, HepG2.2.15 cells were maintained in RPMI media with additions of penicillin and streptomycin (Invitrogen, Carlsbad, Calif.), 10% fetal bovine serum (FBS) (Atlanta Biologicals, Atlanta, Ga.), and 0.1 mg/ml Normocin (InvivoGen, San Diego, Calif.). The cell line HepDE19 was developed upon the principles of the HepAD38 cell line with some modifications. Briefly, HepG2 cells were transfected with plasmid pTet-off (Clontech, Mountain View, Calif.), which expresses tetracycline (tet)-responsive transcriptional activator (tTA), and plasmid pTREHBVDE, in which HBV pgRNA expression is controlled by a cytomegalovirus early promoter with tet responsive element (TRE). Transfected HepG2 cells were selected by G418, colonies were expanded in tet-free medium to induce HBV replication, and viral DNA replication level was determined by southern blot. Cells with highest HBV replication were selected and designated as HepDE19. In this cell line, the start codon AUG of preCore on the 5' end of the integrated 1.3-unit-length HBV genome was removed to prevent HBeAg expression from the transgene, but could be restored from the 3' terminal redundancy of pre-genomic RNA during viral DNA replication and subsequent cccDNA formation. Therefore, HBeAg is only translated from the preCore mRNA transcribed from the episomal cccDNA. HepDE19 cells were maintained in DMEM/F-12 media with penicillin and streptomycin (Invitrogen), 10% FBS, 500 µg/ml G418 (Invitrogen) and 1 µg/ml tetracycline (Sigma-Aldrich, St. Louis, Mo.). HepG2 cells were maintained in media identical to that for HepG2.2.15.

Herpes simplex virus type 1 (HSV1, strain K057) was propagated in Vero cells in DMEM/F-12 media with penicillin, streptomycin and 10% FBS. Bovine viral diarrhea virus (BVDV, strain NADL) was propagated in MDBK cells in DMEM/F-12 media with penicillin, streptomycin, and 10% horse serum (Invitrogen). Viral stock cultures were collected by scraping cell cultures upon observation of full cytopathic effect (CPE), centrifugation, freeze/thawing of cell pellet in appropriate culture media, and titering by plaque assay. For both viruses, stocks were diluted in 10-fold steps and plaque assays were carried out in 6 well dishes, with 1.5% methyl cellulose overlay containing 10% FBS for Vero or 10% horse serum for MDBK. Plaques were visualized by crystal violet staining and counted.

Antibodies used in HBsAg ELISA for screening were as follows: Primary capture antibody was anti-HBV surface antigen mouse monoclonal (Fitzgerald Industries, Concord Mass.); detection antibody was horseradish peroxidase-conjugated anti-surface antigen mouse monoclonal antibody (Abbott Diagnostics, Abbott Park, Ill.). Antibodies used for Western blotting were: anti-HBV preS2 domain rabbit polyclonal (Fitzgerald); anti-human α-1-acid glycoprotein mouse monoclonal (Sigma-Aldrich); anti-human a 1-antitrypsin mouse monoclonal (Bethyl Laboratories, Montgomery, Tex.); anti-actin mouse monoclonal (Chemicon International, Temecula, Calif.); and anti-HA mouse monoclonal (Covance, Berkeley, Calif.). Antibody used for protein dot blot was monoclonal anti-HBsAg antibody (DakoUSA, Carpinteria, Calif.).

Plasmid pNI2.SHA, which expresses HBV S (ayw subtype) with an HA tag on the C terminus in mammalian cells, was a kind gift from Dr. Reinhild Prange, Johannes Gutenberg University, Mainz, Germany. To make the plasmid pTRE-MS, which expresses HBV M and S (subtype ayw, isolate V01460) in mammalian cells, the region of nucleotides nts-3174-1-1980 was amplified by PCR with pfu polymerase (Stratagene, La Jolla, Calif.) from plasmid pUC119CMV-HBV, and cloned into pTRE2 (Clontech). The plasmid pTRE-MSHA, which expresses HBV M and S with HA tag on the C-terminus, was made by replacement of the AvrII-NcoI fragment (nts 650-844) in pTRE-MS with the AvrII-NcoI (nts 941-2168) fragment from pNI2.SHA.

Compound sources and handling. The IHVR small molecule collection consists of 80,288 compounds from the complete libraries of ChemDiv, Inc. (San Diego, Calif.), Asinex Inc. (Winston-Salem, N.C.), Chembridge Inc. (San Diego, Calif.), and Maybridge Inc. (Cornwall, United Kingdom). The compounds were selected from the large libraries of each of these companies through cheminformatic analysis that culled generally reactive compounds, structural motifs known to have non-specific biological activity, cLogP values over 5.0, molecular weight over 500 Daltons, and other criteria. While the ~16,000-compound Chemdiv and Asinex portions of the IHVR library are combinatorial, the majority of the library (~64,000) is highly diverse. Although we have not determined it with precision, the number of different pharmacophores represented in the collection numbers in the thousands. In all, the IHVR library has an average molecular weight of ~350 Daltons and maximum cLogP of 5.0.

Compounds were purchased as dry powder in 96-well format "mother" plates, were resuspended in ultrapure dimethylsulfoxide to a final concentration of 10 mM, and diluted in DMSO into working stock ("daughter") plates at 1 mM. Compounds are stored in covered polypropylene plates at −20° C.

Resynthesis of HBF-0259 and other compounds was carried out by ChemDiv Inc. Analogues of HBF-0259 and other compounds were obtained from ChemDiv, Asinex, Chembridge, and Maybridge.

High throughput assay and compound screen. HBsAg ELISA capture wells were made by incubation of 25 µl of monoclonal anti-HBsAg (clone M701077, Fitzgerald) diluted in binding buffer (0.17% Na2CO3, 0.29% NaHCO3, pH 9.6) to 0.9 mg/ml, in each well of polystyrene 96-well plates. Incubation was at 4° C. overnight, followed by washing twice with 150 µl/well of PBS/0.5% Tween 20 (PBST) with shaking. Capture wells were blocked with 150 µl PBST/2.0% BSA at 37° C. for 1 hr, followed by washing twice as described above. Following the second wash, cell culture supernatants from screening plates were transferred and processed as described below.

Stock cultures of HepG2.2.15 cells were grown to confluence, trypsinized, centrifuged, washed once by resuspension in PBS and centrifugation, and seeded in fresh media in 96-well plates at a density of $5.0 \times 10^4$ cells/well, so as to provide confluent monolayers in media that was free of previously secreted HBV antigens. Each screening plate consisted of 80 compound test wells, 4 wells of cells with 1.0% DMSO only, 4 wells with DMSO and without cells, and 4 wells of cells with DMSO and 1 mM dithiothreitol (DTT) as a non-specific reference inhibitor. Immediately following cell seeding, daughter compound plates were thawed at 37° C., and compounds were added to screening plates by means of automated liquid handling, at a final concentration of 10 µM in 1.0% DMSO. Screening plates were incubated at 37° C. in 5.0% CO2 atmosphere for six days. Following incubation, 150 µl of media from each well was transferred to blocked capture plates, and incubated for 4 days at 4° C. Media was removed, plates were washed, and 25 µl/well of detection antibody (diluted to 0.625 ng/ml, in PBST/2.0% BSA) was added. Plates were incubated at 37° C. for 1 hr., washed twice with 1501/well of PBST, with shaking, and 501/well of BM Blue POD substrate (POD, Roche, Indianapolis, Ind.) was added. Plates were allowed to develop at room temperature a minimum of 20 minutes, and color change was assessed visually. Simultaneously, the cell-containing screening plates were fixed and stained with 50% ethanol/0.5% crystal violet, and overall toxicity of each compound was assessed by visual comparison of stained monolayers in compound wells against negative control wells.

To confirm activity of hit compounds, effective concentration inhibiting 50% of secretion activity ($EC_{50}$) was determined by incubating cells with compounds in duplicate wells, at concentrations from 50 µM to 0.016 µM (in half log steps), carrying out ELISA as described above, determination of absorbance of developed assay plates in a SLT Rainbow spectrophotometer (Tecan US, Research Triangle Park, N.C.) at 650 nm with a reference wavelength of 490 nm, and best fit curve analysis of results with XLfit 4.0 (IDBS; Bridgewater, N.J.). Degree of inhibition was calculated against multiple negative control samples where only DMSO was incubated with cells. In addition each plate had multiple wells containing 1.0 mM DTT as a reference inhibitor. Only curves with R2 values of above 0.5 were considered to produce valid $EC_{50}$ values.

Concentration exhibiting 50% cytotoxicity ($CC_{50}$) was determined by plating cells at $1.0 \times 10^4$ cells/well (20% confluence), to detect inhibition of cell growth as compared with absence of compounds. Cell plates were then incubated with compound dilutions and controls as described above, and addition of 3-[4,5-dimethylthiazol-2-yl]-2,5-diphenyltetrazolium bromide (MTT, Sigma-Aldrich) was added to a final concentration of 0.5 mg/ml. Plates were again incubated at 37° C. for 4 hrs, after which 10% SDS/0.01N HCl was added to each well in a volume equal to the media (100 μl), followed by overnight incubation. Absorbance was read in the Rainbow spectrophotometer at 570 nm (reference wavelength of 630 nm), and analyzed with XLfit 4.0 as described above.

Selective index (SI) for each compound was determined as $SI=CC_{50}/EC_{50}$.

Compound treatment of cells and immunodetection of HBV antigens. HepG2.2.15 were seeded in triplicate in 6-well plates at a density of $1.0 \times 10^6$ cells/35 mm well, so as to provide confluent monolayers in media that was free of previously secreted HBV antigen. Control wells contained 0.5% DMSO, and test wells contained indicated concentrations of compounds in a total of 0.5% DMSO on each plate. Plates were incubated 6 days at 37° C. in 5.0% $CO_2$ atmosphere, after which culture fluids from each sample were collected, centrifuged, and the supernatant was retained. Supernatants were mixed 3:1 with 4×SDS-PAGE loading buffer (200 mM Tris-HCl (pH 6.8), 400 mM DTT, 8% SDS, 0.4% bromophenol blue, 40% glycerol). Cell monolayer from corresponding samples was lysed in 2×SDS-PAGE loading buffer and collected. 20 μl of each sample was boiled for 5 minutes, separated by 10% SDS-PAGE, and transferred onto Biotrace PVDF membrane (Pall Corporation; Pensacola, Fla.). Western blotting was carried out using the WesternBreeze (Invitrogen) reagents according to manufacturer specifications. Signal from adsorbed antibodies was detected by enhanced chemiluminescence (GE Healthcare, United Kingdom), and densitometry of developed films was carried out using ImageJ software (NIH, Bethesda, Md.).

For detection of HBV e antigen (HBeAg), 50 μl of supernatant from each well of HBsAg ELISA plates set up for $EC_{50}$ determination was analyzed utilizing the HBeAg ELISA kit from International Immunodiagnostics (Foster City, Calif.), without final addition of $H_2SO_4$. Absorbance was determined at 650 nm with a reference wavelength of 490 nm.

Southern blotting and particle assay. Intracellular viral core DNA was extracted from compound-treated HepDE19 and HepG2.2.15 cells as described previously (19). Briefly, cells from one 60 mm dish were lysed with 1 ml of lysis buffer (10 mM Tris-HCl pH 8.0, 10 mM EDTA, 1% NP40 and 2% sucrose) at 37° C. for 10 minutes. Cell debris and nuclei were removed by centrifugation and the supernatant was mixed with 250 μl of 35% polyethylene glycol (PEG-8000) containing 1.5 M NaCl. After 1 hour incubation in ice, viral nucleocapsids were pelleted by centrifugation at 12,000 g for 10 min at 4° C., followed by 1 hour digestion at 37° C. in 400 μl of digestion buffer [0.5 mg/ml pronase (Calbiochem, San Diego, Calif.), 0.5% SDS, 150 mM NaCl, 25 mM Tris-HCl pH 8.0, and 10 mM EDTA]. The digestion mixture was extracted twice with phenol, and DNA was precipitated with ethanol and dissolved in TE buffer (10 mM Tris-HCl, pH 8.0, 1 mM EDTA). One sixth of the DNA sample from each plate was resolved by electrophoresis into a 1.5% agarose gel. Gel was then subjected to denaturation in a solution containing 0.5 M NaOH and 1.5 M NaCl, followed by neutralization in a buffer containing 1 M Tris-HCl (pH7.4) and 1.5 M NaCl. DNA was then blotted onto Hybond-XL membrane (GE Healthcare) in 20×SSC buffer. Membranes were probed with an α-32P-UTP (800 Ci/mmol, Perkin Elmer)-labeled HBV minus strand-specific full-length riboprobe. Hybridization was carried out in 5 ml EKONO hybridization buffer (Genotech, St. Louis, Mo.) with 1 hr pre-hybridization at 65° C. and overnight hybridization at 65° C., followed by a 1 hr wash with 0.1×SSC and 0.1% SDS at 65° C. The membrane was exposed to a phosphorimager screen and hybridization signals were quantified with QuantityOne software (Bio-Rad).

For the HBsAg dot blot assay, culture fluids were harvested at indicated time points, centrifuged at 1,000 rpm for 10 min, and stored at 4° C. Forty microliters of supernatant was spotted on nitrocellulose membrane (Schleicher & Schuell/Whatman, Florence Park, N.J.), air dried, soaked in 2.5% formaldehyde/PBS for 30 min, briefly rinsed with water, then soaked in 50% methanol for 30 min. After three 5 minute washes with water, the membrane was blocked and probed with monoclonal anti-HBsAg antibody (DakoUSA, Carpinteria, Calif.), washed, and incubated with an HPR-conjugated secondary antibody. Binding was visualized with an enhanced chemiluminescence detection system (Amersham Pharmacia Biotech).

For the DNA dot blot assay, 400 μl of supernatant was spotted on nitrocellulose, air dried, and the DNA-containing particles were denatured by soaking the membrane for 30 min in 0.2 M NaOH containing 1.5 M NaCl. The filter was then neutralized with 0.2 M Tris-HCl, pH 7.4, containing 1.5 M NaCl for 30 min, washed in TNE buffer (10 mM Tris-HCl, pH 7.4, 150 mM NaCl, 1 mM EDTA) and dried. Viral DNA was detected by hybridization as described above.

The HBV particle assay was performed as previously described (33). Briefly, the viral particles were precipitated from 1 ml clarified culture fluid by addition of PEG-8000 to 10% final concentration, followed by incubation at 4° C. for 1 hr. Precipitates were collected by centrifugation at 925×g for 20 min and dissolved in 40 μl DMEM/F12 medium. The viral particles were fractionated by electrophoresis through nondenaturing 1% agarose gels and transferred to a nitrocellulose filter by blotting with TNE. DNA-containing particles on the filter were then denatured, neutralized, and viral DNA was detected by hybridization as described above.

Transfection and compound treatment. HepG2 cells were seeded into 24 well plates at $1.0 \times 10^5$ cells/well (40-80% confluency). For each transfection condition, media was combined with Fugene 6 transfection reagent (Roche Diagnostics) according to manufacturer recommendations, and incubated 5 min at room temperature. Plasmid DNA was added at 1 μg/ml, and the mixture was incubated at room temperature 30 min. Transfection mixture was then added dropwise to cells at 100 μl/well and incubated overnight at 37° C. The next day, transfection mixture was removed, and fresh media with either 4 μM of HBF-0259 or 0.5% DMSO was added to each well. Cells were thus treated over 6 days with HBF-0259, with media and compound changed at day 3. Following incubation, culture supernatant and cell monolayers were harvested and analyzed for either S-HA or M-HA by Western blot analysis.

Results

Identification of HBF-0259 as an inhibitor of HBV surface antigen secretion. A high-throughput screen of the 80,288 compounds in the IHVR collection was undertaken, using a "sandwich" ELISA designed to quantitatively detect the "a" epitope of HBsAg secreted by HepG2.2.15 cells. The primary screen yielded 1,758 hits, defined as compounds inhibiting secretion by at least 50%. Of these, 1607 were identified by crystal violet staining of cells in the primary screen as sufficiently cytotoxic at 10 µM to have scored as an inhibitor for that reason alone, or did not repeat inhibition of HBsAg secretion when retested at a variety of concentrations (10, 3.6, 1.0, 0.36 µM) with the primary screening assay. The remaining 151 were analyzed by repeating of the primary screening assay with an increased range of compound concentrations (50-0.016 µM) to determine $EC_{50}$, and by MTT assay at the same concentrations to determine $CC_{50}$. These assays were carried out in both HepG2.2.15 and the HepDE19 cell line developed by our group. Of these, 77 were found to have SI values at or above 4.0, and were selected for further investigation. Since the screen scored for the ability to inhibit native "a" epitope secretion as detected by ELISA, we employed Western blotting as a secondary assay to permit analysis of effects upon full length, denatured surface antigen. Thus, secretion of L and M was analyzed from HepG2.2.15 cells treated with 8, 4, 2, 1, 0.5 and 0.25 µM of each compound. Of these, approximately 16 compounds were identified as causing significant, reproducible inhibition of secretion of the large and middle antigens. These compounds were assayed for purity by HPLC/mass spectroscopy. Most were found to consist of at least 90% predicted substance. Based on general predictions for chemical tractability and cost estimates, a tetrahydro-tetrazolo-pyrimidine (specifically, 7-(2 chloro-6-fluoro-phenyl)-5-(4-chorophenyl)-4,5,6,7-tetrahydro-tetrazolo[1,5-a]pyrimidine) referred to as HBF-0259 (FIG. 2A), was chosen for follow-up studies.

Figure 2:
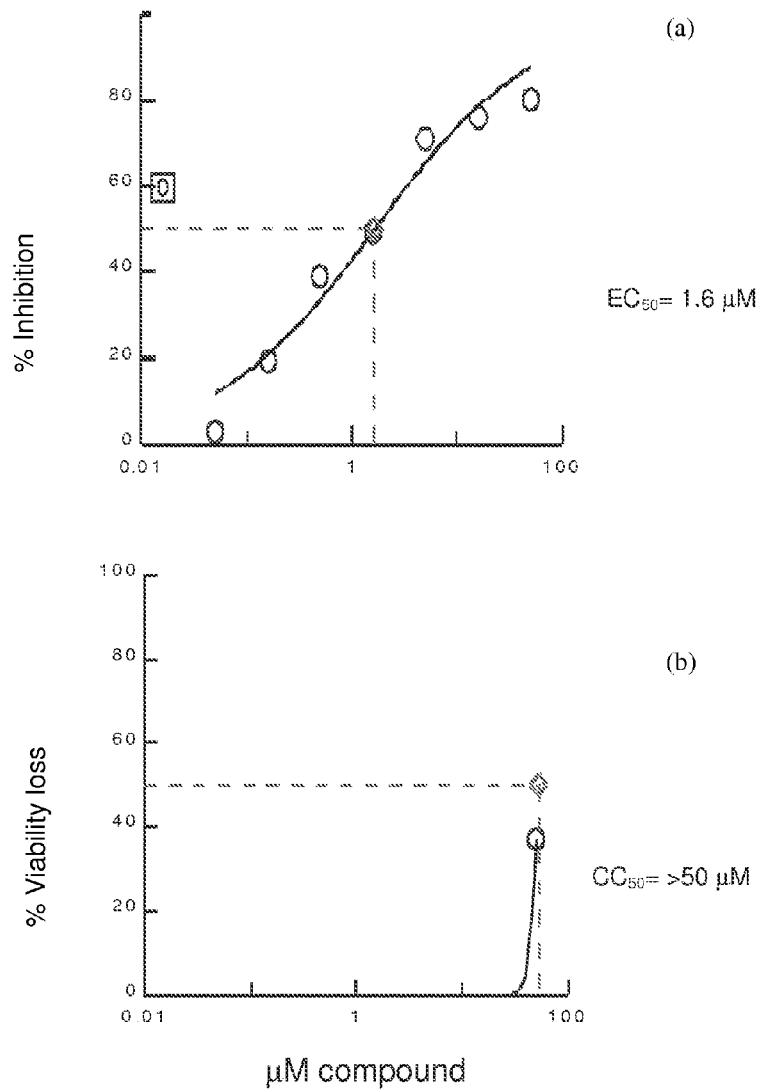
FIGS. 2a-b depict an $EC_{50}$ and $CC_{50}$ determination in HepDE19 cells by HBsAg ELISA and MTT assay, respectively. All data points are average of duplicate wells. Best fit curve and calculation carried out with XLfit 4.0 software, with outliers removed if necessary to generate $R^2$ value above 0.5. Compound concentrations are expressed on a $log_{10}$ scale, and were (left to right) 0.0158, 0.05, 0.158, 0.5, 1.58, 5.0, 15.8, 50.0 µM. Percent inhibition of secretion and percent loss of viability was calculated against addition of DMSO alone, which was scored as 0% inhibition and 0% loss of viability.

HBF-0259 is a selective inhibitor of HBsAg secretion. Using the screening ELISA, we measured the $EC_{50}$ and $CC_{50}$ of HBF-0259. In the HepG2.2.15 cell line, the $EC_{50}$ of HBF-0259 in the primary screening ELISA has been somewhat variable (results not shown), although cytotoxicity has never been observed. This variability (also noted with other compounds) appears to be a property of these cells, and is likely related to the highly variable levels of HBV antigen secretion exhibited by the HepG2.2.15 cell line. Alternatively, in the HepDE19 cell line the $EC_{50}$ for inhibition of surface antigen secretion ranges from 1.1-1.6 µM. While the $CC_{50}$ is >50 µM, yielding a specificity index of at least 31 (FIG. 2B).

The effects of this compound on the secretion and intracellular processing of L and M HBV antigens were assayed by Western blotting of supernatants and whole-cell lysates from treated cells, using an antibody specific for the preS2 region. In HepG2.2.15 cells treated with HBF-0259 at 8.0, 4.0, and 2.0 µM concentrations, both L and M are found in significantly lower amounts in the supernatant of the cells, as compared to a control treated only with the compound solvent (DMSO) alone. Densitometric analysis of this blot indicated that in the 4.0 µM sample, total inhibition of L and M secretion was 58%, yielding an $EC_{50}$ in this assay of 3.0-4.0 µM. In the same samples, levels of α-1-acid glycoprotein (AGP) and a 1-antitrypsin appear to be unaffected by the presence of the compound (FIG. 3A).

Figure 3A:
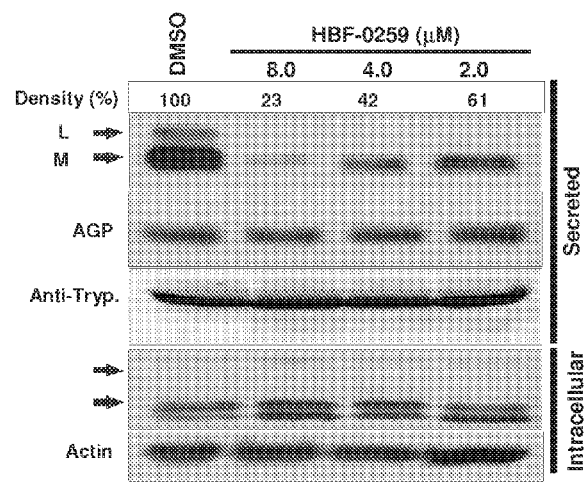
FIGS. 3a-d demonstrate the characterization of HBF-0259 activity by secondary assays. (A) HepG2.2.15 cells were treated, and cell culture supernatants were analyzed by Western blotting for L, M, AGP, and α1-antitrypsin. Whole cell lysates were analyzed by Western blotting for L, M and actin. (B) Culture supernatants from HepG2.2.15 treated with HBF-0259 or DMSO only, as in (A), were analyzed for total HBsAg by dot blot EIA in non-denaturing conditions. (C) Culture supernatants from 2.2.15 cells treated with indicated concentrations of HBF-0259, 1 mM DTT, or DMSO alone were assayed for secreted HBeAg by capture ELISA. Percent inhibition of secretion was calculated by normalizing reading of DMSO-only sample to 100% secretion, or 0% inhibition. (D) Effects on L, M and AGP secretion from HepG2.2.15 cells of extended incubation with HBF-0259, or DMSO alone. Culture supernatants were collected every three days from the third day, up to day 24. Samples were analyzed by Western blotting as in (B)
Figures 3B, 3C:
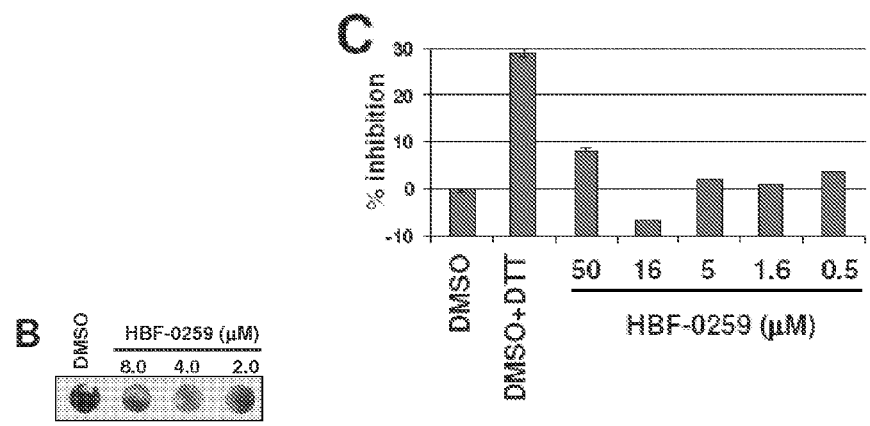

Intracellular levels of L and M and their respective glycoforms do not appear to be reduced, and actually exhibit a slight accumulation in the presence of the compound, especially of the non-glycosylated form of M (p30, FIG. 3A). Effects on total S, M, and L secretion were also assessed by dot blot EIA with an anti-S ("a" epitope) antibody, and indicated a notable reduction of the total signal in culture supernatant from HBF-0259-treated HepG2.2.15 cells (FIG. 3B), thus corroborating the results observed with the primary screening ELISA, and with L and M-specific Western blotting. Interestingly, HBF-0259 did not affect HBeAg secretion in HepG2.2.15 (FIG. 3C), as compared to treatment with DTT. Because HBeAg secretion is distinct from that of HBV subviral particles, and the extracellular levels of two non viral proteins are also unaffected, HBF-0259 appears to specifically target only secretion of S, M, and L-containing particles.

Figure 3D:
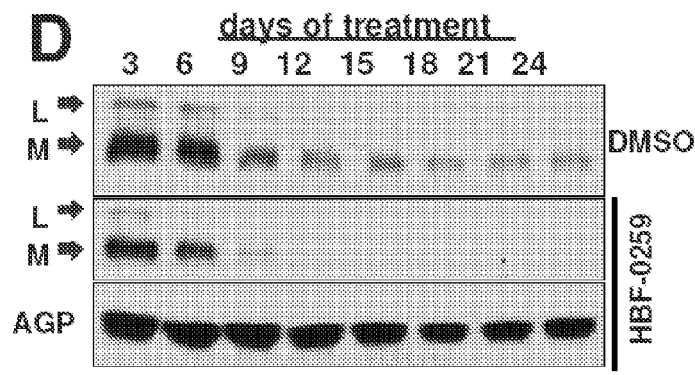

To investigate the effects of long-term HBF-0259 treatment on secretion of subviral particles, HepG2.2.15 cells were plated at high density conditions and incubated with 4.0 µM compound in 0.5% DMSO, or 0.5% DMSO alone, for 24 days. Samples of media were collected every three days, and media and compound/DMSO were refreshed at those intervals. Samples were analyzed by Western blotting for L, M, and AGP. In the absence of compound, there was a marked decrease in the levels of L and M after six days of incubation, stabilizing after 18 days. In the presence of compound, levels of L and M secretion were attenuated as early as three days, and became undetectable after 9 days, while secretion of AGP remained relatively unaffected (FIG. 3D). These observations indicate that HBF-0259 may be potentiating a tendency on the part of the cells to attenuate secretion of HBV subviral particles over an extended period, and that the HBV secretion pathway does not become habituated to the presence of the inhibitor.

HBF-0259 reduces HBV particle secretion without affecting viral replication. To determine the effects of this compound on intracellular viral replication, HepDE19 cells were subjected to tetracycline withdrawal to permit synthesis of HBV pregenomic and mRNAs, capsid assembly and DNA synthesis by reverse transcription. After 7 days, HBF-0259 was added at 2.0, 4.0 and 8.0 µM, or DMSO alone, for an additional 6 days in the absence of tet, with changes of media and fresh compound added after three days. Cell monolayers and culture supernatants were then harvested. Intracellular viral replicative intermediates (rc and ss DNA) were analyzed by Southern blot assay. The culture supernatants were subjected to separation by non-denaturing agarose gel electrophoresis and probed by DNA hybridization for virion DNA. In addition, supernatants were also analyzed by dot blotting and DNA hybridization.

We observed no changes in the levels of intracellular DNA in the presence of HBF-0259 (FIG. 4, top panel), indicating that the compound has no effect on the steps of viral genomic replication which are reproduced in this HepG2-derived stably-transfected system, namely the posttranscriptional events of HBV replication. A similar analysis of viral genomic replication in HepG2.2.15 cells yielded the same result (not shown). However, we cannot exclude the possibility that the compound may affect the steps of replication that are not reproduced here, specifically virus binding to receptor, entry and uncoating. However, inhibition of pre-transcriptional steps cannot affect envelope secretion in either the HepG2.2.15 or the HepDE19 systems, and so would be unrelated to the observations reported herein.

Figure 4:
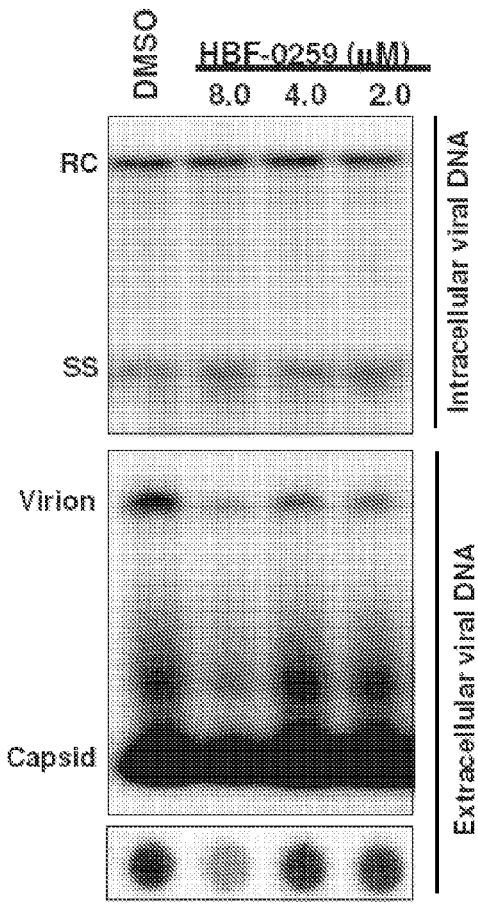
FIG. 4 demonstrates the effects of HBF-0259 treatment on intracellular HBV DNA synthesis, and secretion of HBV DNA containing particles. HepDE19 cells were withdrawn from tetracycline for seven days, after which treatment with HBF-0259 or DMSO was initiated and continued for six days. Cell monolayers and culture supernatants were harvested and processed for intracellular core associated DNA (top panel), secreted particles (particle assay, middle panel), and total extracellular viral DNA (bottom panel)

In contrast, treatment of HBF-0259 had a significant inhibitory effect on levels of virion-associated DNA secreted from these cells, as demonstrated by particle assay and DNA dot blot (FIG. 4, middle and bottom panels, respectively). This observation is in agreement with the inhibition of secretion of the envelope proteins that comprise subviral particles. A slight lessening of "naked" HBV capsid was also observed. Although commonly seen, the mechanism whereby these nucleocapsids exit the cell is unknown, but this effect most likely corroborates the observed inhibition of intact virus levels. Therefore, the stage of the intracellular HBV life cycle targeted by HBF-0259 appears to be secretion of enveloped particles, at a step occurring downstream of capsid assembly and reverse transcription.

HBF-0259 inhibits secretion of transiently expressed HBV envelope proteins. To corroborate our observations in the stably-expressing HepG2.2.15 and HepDE19 cell systems, we employed transient transfection of the parental HepG2 cell line with the plasmid constructs pNI2.SHA and pTRE-MSHA, which encode the S and M proteins with C-terminal HA epitope tags, respectively. Due to inherent cytotoxicity of exogenously expressed L, that protein was not used in these experiments. Compound treatment was initiated immediately following transfection, and continued for a total period of 48 hrs, when both media and cells monolayers were harvested and analyzed by Western blotting using both anti-HA (for S and M) and anti-pre-S2 (for M) antibodies. As shown in FIG. 5A, incubation with 4.0 µM HBF-0259 resulted in a significant decrease in the levels of secreted S-HA; intracellular levels of S-HA were not reduced, and exhibited an accumulation of the non-glycosylated form of S-HA (p24). In addition, a "smearing" of the intracellular S-HA signal, seen in the DMSO-treated sample, was notably absent from the HBF-0259-treated sample (bracketed, FIG. 5A); it is likely that this observation represents oligomerization of S, which has been observed even under mildly reducing gel conditions (i.e. presence of DTT). Oligomerization of S occurs during transport through the endoplasmic reticulum, suggesting that HBF-0259 may prevent transport of HBsAg through the secretory pathway.

A reduction in M-HA secretion was observed by detection with both anti-HA and anti-pre-S2 antibodies, although the level of inhibition between these two detection conditions varied (FIG. 5B). Similar to S, analysis of intracellular M indicates that HBF-0259 causes the accumulation of the non-glycosylated (p30) and also the single glycosylated (p33) forms of M-HA, suggesting that HBF-0259 may be affecting full glycosylation of M-HA. Overall, data presented in FIG. 4 indicate that the inhibitory effects of HBF-0259 on HBV subviral particles are independent of non-envelope viral proteins and viral replication, and that the compound may be inhibiting transport of HBsAg through the secretory pathway at a pre-glycosylation or early glycosylation step.

Selective antiviral spectrum of HBF-0259. Because the exact mechanism of action of HBF-0259 is yet unknown, it is possible that this compound may have a general activity that may be extended to other viruses. To ascertain the potential for HBF-0259 as a general antiviral compound, we tested its effects on cell-to-cell spread of wild-type herpes simplex virus type 1 (HSV1, of the herpesviridae), strain K057, and bovine viral diarrhea virus (BVDV, of the flaviviridae), strain NADL. HSV-1 was used to infect the Vero cell line, and BVDV was used on the MDBK cell line. For both viruses, cells were mock-infected, or infected at varying multiplicities of infection (MOI) of 1.0, 0.1, 0.01, and 0.001, either in the presence of 5 µM HBF-0259 or DMSO alone. Cells monolayers at each MOI condition were inspected by microscopy for evidence of cytopathic effect (CPE), and were harvested on the day on which full CPE was observed in the DMSO-only control. Samples that were mock infected, or in which full CPE was not observed, were harvested at 4 days post-infection in BVDV plates and 9 days post infection in HSV-1 plates. At harvest, cell viability was determined by MTT assay as a percentage of viability of the mock-infected, DMSO-only sample. As depicted in FIG. 6, panels A and C, HBF-0259 did not protect cells infected at MOI 1.0 or 0.1 from full CPE for either virus. However, in cells infected with MOI 0.01 and 0.001 BVDV, the presence of HBF-0259 did correlate with a slight decrease in the level of BVDV-induced CPE, as opposed to DMSO alone (FIG. 6A). This effect was not observed in the HSV-1 infected samples (FIG. 6C).

For both virus systems, the effect of HBF-0259 on plaque size, and therefore on efficiency of cell-to-cell spread, was determined by plating approximately 100 plaque forming units/35 mm well on MDBK and Vero cell monolayers grown to approximately 75% confluency. Cells were overlayed with appropriate media containing methylcellulose, and containing 8.0, 4.0, or 2.0 µM HBF-0259, or DMSO alone. Plaque development was monitored visually and by microscopy, and was allowed to proceed to the point where plaque size was readily observable. Overlay was then removed and cells were fixed and stained with crystal violet. The presence of HBF-0259 at all three concentrations seemed to result in only a very slight size reduction of BVDV plaques as compared to DMSO alone (FIG. 6B). The size of HSV1 plaques was unaffected by the compound (FIG. 6D); because wild type HSV-1 spreads primarily by extracellular virus rather than by syncytia formation, these results indicate that HBF-0259 has no ability to restrict efficiency of cell-to-cell spread of HSV 1. However, the compound may be able to weakly inhibit efficiency of BVDV cell-to-cell spread, as evidenced by protection of a monolayer from CPE at very low MOI (albeit not at MOI where 10% or more of the cells would be infected).

Inhibitory Activity of Structural Analogues of HBF-0259. We obtained samples of 10 analogues of HBF-0259, all of which vary in the aromatic ring substitutions at carbon 5 and carbon 7 in the tetrahydro-tetrazolo-pyrimidine ring. For simplicity, we refer to the carbon 5 substituent as $R_1$ and the carbon 7 substituent as $R_2$. As illustrated in FIG. 7, 6 of the 10 analogues exhibited $EC_{50}$s below 50 µM, with 4 of the compounds having no detectable inhibition, or $EC_{50}$s above 50 µM. Cytotoxicity of the active analogues was also relatively low; no compound had a $CC_{50}$ lower than 37.5 µM (i.e., compound 4567), although SI values were calculated as very low for compounds 2160, and 4564 due to relatively high $EC_{50}$s.

Discussion

HBF-0259 is a specific inhibitor of HBV particle secretion. Our group carried out a high throughput screen of a carefully-assembled small molecule library in an effort to identify novel compounds that would inhibit the egress of viral antigens from the HBV-replicating HepG2.2.15 cell line. The screening campaign was specifically directed to identify inhibitors of this particular step of the HBV life cycle, and to minimize identification of compounds affecting other steps. For example, because the envelope proteins are primarily expressed from the integrated HBV transgene in these cells, rather than established cccDNA templates, our screening assay would not have scored inhibitors of viral genomic replication, or inhibitors of HBV DNA nuclear transport and cccDNA establishment. Similarly, compounds affecting core protein dimerization and general capsid assembly would have not been identified, since secretion of subviral particles (which comprise the vast majority of extracellular HBV surface antigen, as compared to Dane particles) is independent of capsid assembly. Through secondary assays, we eliminated compounds with significant cytotoxicity, and confirmed the activity of many of the hits scored in the primary screen. Finally, after further investigation we focused on the compounds we judged to be acting in an HBV-specific manner. Of these, HBF-0259 is the first to be reported. In tissue culture, it has an $EC_{50}$ in the low micromolar range, and a $CC_{50}$ of over 50 µM, constituting a "window" large enough to suggest that this compound's inhibitory activity does not stem from indirect effects on cellular metabolism. Its activity is persistent over lengthy incubations, it appears to act on all three HBV surface antigens, and on subviral as well as infectious particles. In direct contrast to the recently reported activity of ellagic acid, it does not inhibit secretion of HBeAg, singling out its effects to HBV surface antigen. Initial observations of its effects on intracellular non-glycosylated and glycosylated forms of HBsAg suggest that it blocks secretion at an early step in the pathway. It has no effect on HBV DNA synthesis, and hence cannot be affecting capsid assembly or retrotranscription. It has little or no effect on the ability of two unrelated viruses to spread from cell-to-cell. Finally, limited SAR studies suggest that the activity of HBF-0259 may be extended to some other members of this class of molecules, indicating that exploring the chemistry of this compound may lead to optimization of its activity. Overall, HBF-0259 is a novel inhibitor of a crucial step in the HBV life cycle and in chronic disease progression.

HBF-0259 is a novel chemical class to exhibit anti-HBV activity. With the exception of interferon, all of the FDA-approved antiviral drugs for hepatitis B treatment are nucleoside and nucleotide-based polymerase inhibitors. Furthermore, experimental anti-HBV compounds such as Bay 41-4109 and the analogous heteroaryldihydropyrimidines (HAPs), bis-ANS, and the phenylpropenamide derivatives AT-61 and AT-130 are not functionally or structurally related to HBF-0259. Ellagic acid, and interesting compound derived from extracts of the plant Phyllanthus urinaria, appears to specifically inhibit secretion of HBeAg in vivo and in vitro, without affecting secretion of surface antigen, or HBV genomic replication. Our group has reported the inhibitory effects on the secretion of HBV secretion and other viral glycoproteins of the iminosugar derivatives of deoxynojirimicim (DNJ) and related glycolipids, which work primarily by competitive inhibition of α-glucosidase and also by stimulation of intrinsic interferon response. To this collection of approved and experimental antivirals, we add the tetrahydropyrimidine class of compounds represented by HBF-0259, which have not been previously reported to have antiviral activity.

The significance of this new chemical class of HBV inhibitors can be divided into the implications for therapy, and its possible utility in uncovering novel aspects of HBV particle assembly and secretion. Antigen secretion inhibitors may prove useful in ameliorating antigenemia in chronic HBV patients. This clinical endpoint may then make it possible to employ immunotherapy (i.e. vaccination) to reduce, or perhaps even eliminate, the population of infected hepatocytes in the liver. Reduction of antigenemia in the WHV infection model has yielded an increase in anti-HBV cellular immune function and antibody titers. Secretion inhibitors and immunotherapy, in combination with interferon and/or polymerase inhibitors, may function as an anti-HBV cocktail that would effectively reduce both intracellular viral replication, and levels of circulating antigen in the form of both infectious and subviral particles.

Studies of the mechanism of action. HBF-0259 may also prove to be a useful tool in furthering understanding of HBV assembly and secretion. Unlike the a-glucosidase inhibitors, HBF-0259 does not appear to affect post-glycosylation processing of the HBV envelope proteins. In addition, we observe a distinct intracellular accumulation of non-glycosylated or early-glycosylated forms of the envelope proteins, whereas the inhibition of secretion effected by the iminosugars causes accelerated proteosomal processing of M. This distinction suggests that HBF-0259 functions through a different mechanism than DNJ and its derivatives, and is of investigational interest for that reason alone.

A principal distinguishing characteristic of this compound is a remarkable degree of specificity in its effects on HBV antigen secretion. It has negligible cytotoxicity at active concentrations; it does not inhibit secretion of at least two abundant cellular glycoproteins; it does not affect the phenotype of two unrelated enveloped virus families that also encode glycoproteins; and, surprisingly, it does not inhibit secretion of HBeAg, an HBV glycoprotein that is not a structural virion or subviral particle component. Although the exact mechanism of action of HBF-0259 remains to be elucidated, these observations suggest that its effects occur though a direct action on either the HBV viral and subviral particles themselves, the antigens they contain, or upon cellular processes or factors that are uniquely required for secretion of these particles.

Optimization of HBF-0259. Chemical tractability was a criteria that we addressed when deciding which active compounds identified in the screen would be further investigated. The substituted tetrahydro-tetrazolo-pyrimidine structure of HBF-0259 is amenable to most modifications for structural optimization. In our initial attempts to do so, a variety of analogues with different substitutions in the tetrahydropyrimidine ring were tested in the primary screening assay; some compounds retained activity, indicating that the HBF-0259 structure is indeed the basis for the inhibition of HBV antigen secretion. Also, toxicity of the series did not increase appreciably, suggesting that there is a high threshold for modifications before any non-specific adverse effects are seen.

A salient feature of HBF-0259 is the presence of two chiral centers, at carbon 5 and carbon 7 of the tetrahydropyrimidine ring. Because it is likely that only one of the stereoisomers is biologically active, it is possible that the $EC_{50}$ of this compound may actually be four times lower than our determinations for either HBF-0259 or any of the analogues that we have tested, assuming approximately equal portions of each isomer. These points are addressed two ways: 1) Separation of the mixture by chiral chromatography, with subsequent testing of the isolated stereoisomers in our primary ELISA assay, and 2) Synthesis of analogues of IHVR modified by insertion of double bonds into the tetrahydropyrimidine ring to reduce or eliminate chirality and tested. Through these approaches, we can determine both the identity of the active stereoisomer, and the importance of the chirality to the biological activity.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for treating a hepatitis B virus in a patient comprising administering an effective amount of a composition to a patient in need thereof comprising:
   (a) an effective amount of a compound selected from the group consisting of Formulas I, II, III, and mixtures thereof;

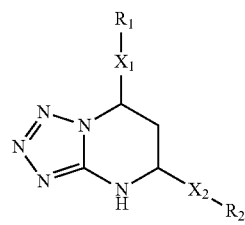

(I)

-continued

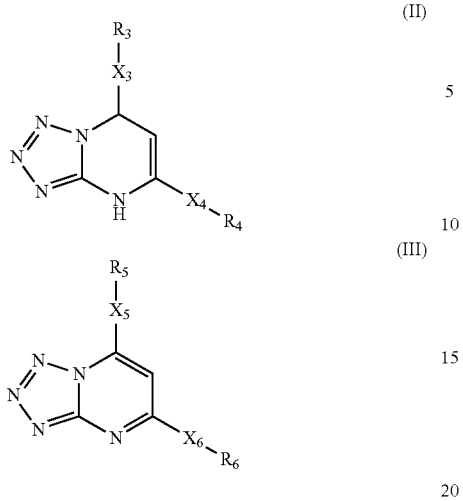

wherein $R_1$, $R_2$, $R_3$, $R_4$, $R_5$, and $R_6$ each independently represent a phenyl or Het, wherein each phenyl or Het is optionally substituted with at least one substitutuent independently selected from the group consisting of alkyl, cycloalkyl, acyl, aryl, halo, $OR_a$, trifluoromethoxy, trifluoromethyl, $NO_2$, $NR_aR_b$, cyano, $CONR_aR_b$, and $CO_2R_a$;

$X_1$, $X_2$, $X_3$, $X_4$, $X_5$, and $X_6$ are selected from the group consisting of a bond, a saturated alkylenegroup and an unsaturated alkylenegroup;

$R_a$ and $R_b$ are each independently H, alkyl, cycloalkyl, alkanoyl, alkanoyloxy,or aryl, or $R_a$ and $R_b$ together with a nitrogen to which they are attached form a Het; and (b) a pharmaceutically acceptable carrier.

2. A method for treating a hepatitis B virus in a patient in need thereof comprising administering to said patient an effective amount of a compound selected from the group consisting of formula I, II, III, and mixtures thereof that reduce the serum level of hepatitis B surface antigen (HBsAg) in said patient, said formula I, II, and III defined as follows:

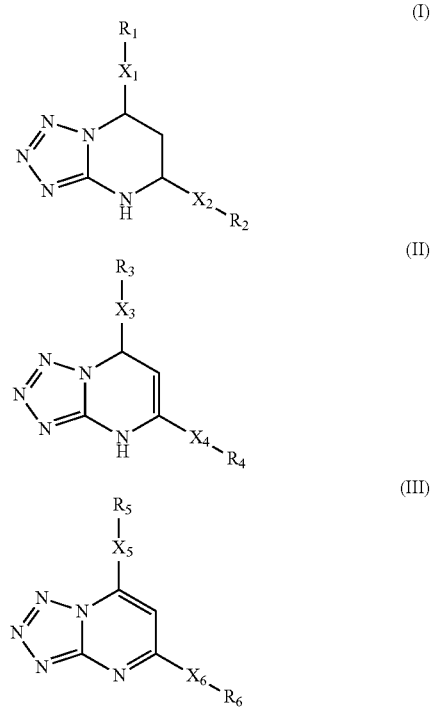

wherein $R_1$, $R_2$, $R_3$, $R_4$, $R_5$, and $R_6$ each independently represent a phenyl or Het, wherein each phenyl or Het is optionally substituted with at least one substitutuent independently selected from the group consisting of alkyl, cycloalkyl, acyl, aryl, halo, $OR_a$, trifluoromethoxy, trifluoromethyl, $NO_2$, $NR_aR_b$, cyano, $CONR_aR_b$, and $CO_2R_a$;

$X_1$, $X_2$, $X_3$, $X_4$, $X_5$, and $X_6$ are selected from the group consisting of a bond a saturated alkylenegroup and an unsaturated alkylenegroup;

$R_a$ and $R_b$ are each independently H, alkyl, cycloalkyl, alkanoyl, alkanoyloxy, or aryl, or $R_a$ and $R_b$ together with a nitrogen to which they are attached form a Het.

* * * * *

UNITED STATES PATENT AND TRADEMARK OFFICE
CERTIFICATE OF CORRECTION

PATENT NO. : 8,609,668 B2  
APPLICATION NO. : 12/299532  
DATED : December 17, 2013  
INVENTOR(S) : Cuconati et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1155 days.

Signed and Sealed this
Twenty-second Day of September, 2015

Michelle K. Lee
*Director of the United States Patent and Trademark Office*